United States Patent
Meyerson et al.

(10) Patent No.: US 12,303,455 B2
(45) Date of Patent: May 20, 2025

(54) THERAPEUTIC TECHNIQUE USING ELECTRICAL IMPEDANCE SPECTROSCOPY

(71) Applicant: Hill-Rom Services, Inc., Batesville, IN (US)

(72) Inventors: Craig M. Meyerson, Syracuse, NY (US); Gene J. Wolfe, Pittsford, NY (US)

(73) Assignee: Hill-Rom Services, Inc., Batesville, IN (US)

( * ) Notice: Subject to any disclaimer, the term of this patent is extended or adjusted under 35 U.S.C. 154(b) by 907 days.

(21) Appl. No.: 17/443,065

(22) Filed: Jul. 20, 2021

(65) Prior Publication Data

US 2022/0031564 A1 Feb. 3, 2022

Related U.S. Application Data

(60) Provisional application No. 62/706,151, filed on Aug. 3, 2020.

(51) Int. Cl.
*A61H 31/00* (2006.01)
*A61H 23/00* (2006.01)
*A61H 23/02* (2006.01)

(52) U.S. Cl.
CPC ........... *A61H 31/00* (2013.01); *A61H 23/006* (2013.01); *A61H 23/02* (2013.01);
(Continued)

(58) Field of Classification Search
CPC ...... A61H 31/00; A61H 23/006; A61H 23/00; A61H 23/02; A61H 2201/1621;
(Continued)

(56) References Cited

U.S. PATENT DOCUMENTS 3,447,071 A * 5/1969 Beckman .................. G01K 7/40
313/146
6,602,201 B1 * 8/2003 Hepp .................. A61B 5/02028
600/526

(Continued)

FOREIGN PATENT DOCUMENTS

AU 2015100881 A4 8/2015
CA 2 912 078 A1 5/2016
(Continued)

OTHER PUBLICATIONS

Baarends et al., "Bod-water compartments measured by bio-electrical impedance spectroscopy in patients with chronic obstructive pulmonary disease," Clinical Nutrition, vol. 17, pp. 15-22 (1998).

(Continued)

*Primary Examiner* — Timothy A Stanis
*Assistant Examiner* — Tyler A Raubenstraw
(74) *Attorney, Agent, or Firm* — Merchant & Gould P.C.

(57) ABSTRACT

Systems and methods of monitoring medical therapies performed by wearable devices using electrical probes. In one example, a pulmonary physiotherapy device implements a treatment protocol function gated and modulated using electrical impedance sensors and metrics. The sensors operate to measure electrical impedance of bodily tissue. An electronic controller controls operation of the wearable device. The medical therapy can be modified based on the impedance measurements to maximize efficacy.

16 Claims, 9 Drawing Sheets

(52) U.S. Cl.
CPC ............... *A61H 2201/1621* (2013.01); *A61H 2201/165* (2013.01); *A61H 2201/5007* (2013.01); *A61H 2230/655* (2013.01)

(58) Field of Classification Search
CPC ...... A61H 2201/165; A61H 2201/5007; A61H 2230/655; A61H 2205/084; A61H 9/00; A61H 7/004; A61H 2031/002; A61H 9/0007; A61H 9/0078; A61M 16/0006; A61B 5/053; A61B 5/063; A61B 5/068; A61B 5/08; A61B 5/0816; A61B 5/085; A61B 5/087; A61B 5/256; A61B 5/4869; A61B 5/6802; A61B 5/6805; A61B 5/6804; A61B 7/003; A61B 2560/0468; A61B 2562/0209; A61B 5/0809
See application file for complete search history.

(56) References Cited

U.S. PATENT DOCUMENTS

| | | | |
|---|---|---|---|
| 6,676,614 B1 * | 1/2004 | Hansen | A61H 23/04 601/44 |
| 6,690,181 B1 | 2/2004 | Dowdeswell et al. | |
| 7,162,296 B2 | 1/2007 | Leonhardt et al. | |
| 7,787,946 B2 | 8/2010 | Stahmann et al. | |
| 7,945,302 B2 | 5/2011 | McAdams | |
| 8,032,229 B2 | 10/2011 | Gerber et al. | |
| 8,257,288 B2 | 9/2012 | Hansen et al. | |
| 9,002,427 B2 * | 4/2015 | Tupin, Jr. | A61B 5/087 600/407 |
| 9,017,256 B2 * | 4/2015 | Gottesman | A61B 5/486 600/300 |
| 9,242,115 B2 * | 1/2016 | Freeman | A61N 1/0452 |
| 9,439,599 B2 * | 9/2016 | Thompson | G16H 40/67 |
| 9,597,257 B2 * | 3/2017 | Halperin | A61H 31/006 |
| 10,016,335 B2 | 7/2018 | Hansen et al. | |
| 10,055,548 B2 * | 8/2018 | Jorgenson | G16H 40/63 |
| 10,226,187 B2 * | 3/2019 | Al-Ali | A61B 5/447 |
| 10,285,617 B2 * | 5/2019 | Toth | A61B 5/25 |
| 10,307,074 B2 * | 6/2019 | Ward | A61B 5/0537 |
| 10,660,531 B1 * | 5/2020 | Libove | A61B 5/369 |
| 10,660,555 B2 * | 5/2020 | Wang | A61B 5/14532 |
| 10,667,717 B2 * | 6/2020 | Freeman | A61B 5/0809 |
| 10,772,793 B2 * | 9/2020 | Paradis | A61H 31/006 |
| 10,828,007 B1 * | 11/2020 | Telfort | A61B 7/02 |
| 11,724,130 B2 * | 8/2023 | Lewis, Jr. | A61N 7/00 601/2 |
| 11,833,096 B2 * | 12/2023 | Brenner | A61H 23/0245 |
| 11,998,303 B2 * | 6/2024 | Sarkar | A61B 5/0205 |
| 2004/0153009 A1 * | 8/2004 | Horzewski | A61H 23/0236 601/2 |
| 2008/0082018 A1 * | 4/2008 | Sackner | A61B 5/369 600/529 |
| 2008/0108914 A1 * | 5/2008 | Brouqueyre | A61H 9/0078 601/2 |
| 2008/0287770 A1 * | 11/2008 | Kurzweil | A61B 5/0295 600/388 |
| 2009/0309578 A1 * | 12/2009 | Cochran | A61B 5/1126 336/84 R |
| 2010/0182025 A1 * | 7/2010 | Riley | A61B 5/6892 324/727 |
| 2011/0213274 A1 * | 9/2011 | Telfort | A61B 7/003 600/586 |
| 2011/0257551 A1 * | 10/2011 | Banet | A61B 5/0816 600/534 |
| 2013/0289456 A1 * | 10/2013 | Chang Guo | A61H 9/0078 601/149 |
| 2014/0005579 A1 * | 1/2014 | Drlik | A61H 23/0218 601/111 |
| 2014/0155732 A1 | 6/2014 | Patz et al. | |
| 2014/0323816 A1 * | 10/2014 | Soderberg | A61G 7/0527 600/300 |
| 2015/0051469 A1 * | 2/2015 | Seppa | A61B 5/091 600/384 |
| 2015/0265221 A1 | 9/2015 | Flanagan et al. | |
| 2015/0352367 A1 * | 12/2015 | Quan | A61B 5/7253 601/41 |
| 2016/0128632 A1 * | 5/2016 | Wiebe | A61B 5/0015 340/870.07 |
| 2016/0287170 A1 * | 10/2016 | Ronen | A61B 5/7235 |
| 2016/0317383 A1 * | 11/2016 | Stanfield | A61H 3/061 |
| 2016/0361228 A1 * | 12/2016 | Paradis | A61H 31/005 |
| 2017/0027813 A1 * | 2/2017 | Bobey | A61H 9/0078 |
| 2017/0035637 A1 * | 2/2017 | DeVliegar | A61H 23/0218 |
| 2017/0290732 A1 | 10/2017 | Palomäki et al. | |
| 2018/0055442 A1 * | 3/2018 | Freeman | A61N 1/046 |
| 2018/0092804 A1 * | 4/2018 | Hunt | A61N 1/39044 |
| 2018/0177483 A1 * | 6/2018 | Ye | A61H 23/004 |
| 2018/0272147 A1 * | 9/2018 | Freeman | G16H 50/30 |
| 2019/0015233 A1 * | 1/2019 | Galloway | B25J 15/12 |
| 2019/0167502 A1 * | 6/2019 | DeVlieger | A61H 23/0218 |
| 2019/0192066 A1 * | 6/2019 | Schoess | A61B 5/6813 |
| 2019/0274580 A1 | 9/2019 | Krammer et al. | |
| 2019/0274919 A1 * | 9/2019 | Lee | A61H 23/04 |
| 2019/0282113 A1 * | 9/2019 | Wang | A61B 5/363 |
| 2019/0328268 A1 * | 10/2019 | Woo | A61B 5/0205 |
| 2019/0328276 A1 * | 10/2019 | Woo | A61B 5/0809 |
| 2019/0328277 A1 * | 10/2019 | Woo | A61B 5/6822 |
| 2019/0357776 A1 * | 11/2019 | Carreon | A61B 5/02055 |
| 2020/0069953 A1 * | 3/2020 | Finch | A61N 1/046 |
| 2020/0138335 A1 | 5/2020 | Stender | |
| 2020/0329977 A1 * | 10/2020 | Freeman | A61M 16/0051 |
| 2020/0383647 A1 * | 12/2020 | Freeman | A61B 5/02055 |
| 2020/0386728 A1 * | 12/2020 | Potyrailo | G01N 31/223 |
| 2021/0076978 A1 * | 3/2021 | Kandori | A61B 5/113 |
| 2023/0039829 A1 * | 2/2023 | Iope | A61B 5/086 |

FOREIGN PATENT DOCUMENTS

| | | | | |
|---|---|---|---|---|
| CN | 106463040 A | 2/2017 | | |
| CN | 108135489 A | 6/2018 | | |
| CN | 110123321 A | 8/2019 | | |
| EP | 2 762 062 A1 | 8/2014 | | |
| EP | 3 549 515 A1 | 10/2019 | | |
| RU | 2012158254 A | 7/2014 | | |
| WO | WO-2007133557 A2 * | 11/2007 | ........... A61H 9/0078 | |
| WO | WO-2014037874 A1 * | 3/2014 | ........... A61B 5/0059 | |
| WO | 2018226999 A1 | 12/2018 | | |

OTHER PUBLICATIONS

Extended European Search Report for Application No. 21189024.9 mailed Jan. 12, 2022.

* cited by examiner

THERAPEUTIC TECHNIQUE USING ELECTRICAL IMPEDANCE SPECTROSCOPY

BACKGROUND

The measurement of the electrical impedance of biological tissues is known to hold significant promise for characterizing and diagnosing a vast myriad of clinical conditions and disease processes. It is known that different tissues have a characteristic impedance fingerprint. This fingerprint can be used in clinical interpretation.

SUMMARY

Embodiments of the disclosure are directed to monitoring medical therapies performed by wearable devices using electrical impedance sensors. The sensors operate to measure electrical impedance of bodily tissue. The medical therapy can be modified based on the impedance measurements to maximize efficacy.

In one aspect, a medical therapy system comprises: a wearable medical therapy device comprising: one or more electromechanical components configured to administer a medical therapy to a patient; a plurality of impedimetric sensors configured to monitor the medical therapy, each of the impedimetric sensors comprising a source, a guard ring, and a probe; an electronic controller and a power source operatively connected to the one or more electromechanical components and plurality of impedimetric sensors, for generating and modulating an electrical signal to energize the one or more electromechanical components and plurality of impedimetric sensors; and a computing device in communication with the wearable medical therapy device, the computing device comprising: a processing device; and a memory device comprising: a data store comprising a lookup table of physiometric parameters; and instructions that, when executed by the processing device, cause the computing device to: a) determine a preliminary frequency range based on physiometric parameters of the patient and the lookup table; b) communicate instructions to the plurality of impedimetric sensors to sweep the preliminary frequency range; c) receive impedimetric measurements from the impedimetric sensors and plot them against their respective frequencies; d) identify a resonant point and feature and shape characteristics of a curve generated from the patient in the plot; d) communicate instructions to the wearable medical therapy device to initiate a therapy protocol based on the curve; e) monitor, with the plurality of impedimetric sensors, efficacy of the therapy protocol by measuring impedance over time; f) create a measurement matrix representing impedance measurements between pairs of the impedimetric sensors; g) analyze the measurements to determine efficacy of the therapy protocol for a physiological area of the body associated with a sensor location; h) based on the results of step g, modulate or modify the therapy protocol; and i) return to step e) and repeat until therapy has reached a measureable metric or concluded.

In another aspect, a method of monitoring treatment efficacy of a body-worn medical therapy device comprises a) determining a preliminary probe frequency range based on physiometric parameters of the patient and the lookup table; b) communicating instructions to the plurality of impedimetric sensors to sweep the preliminary probe frequency range in a vernier technique; c) identifying a resonant point for the patient and determining an order of a curve for the impedance measurements; d) communicating instructions to the wearable thorax percussion device to initiate a therapy protocol, the therapy protocol comprising at least a duration and an intensity; e) monitoring, with the plurality of impedimetric sensors, respiration cycles of the patient and efficacy of the therapy protocol by measuring impedance over time, segmenting into analysis periods that coincide with the respiration cycles of the patient, and recording impedance measurements during peak volume of end inspiration; f) creating a measurement matrix representing impedance measurements between pairs of the impedimetric sensors, g) analyzing the measurements to determine efficacy of the therapy protocol for a physiological area of the thorax associated with a sensor location; h) based on the results of g, modulating or modifying the therapy protocol by adjusting one or more of duration and intensity; and i) returning to step e) and repeating until therapy has reached a measurable metric or concluded.

In yet another aspect, a pulmonary physiotherapy system comprises: a wearable thorax percussion device for dislodging mucous buildup in the airways of a human patient, the device comprising: a garment fitting over a thorax of the patient; at least one frame element comprising a flat, rigid layer attached to an external surface of the garment; a plurality of electromechanical actuators retained by the at least one frame element, wherein the electromechanical actuators are positioned to provide intermittent percussion to the thorax; and an electronic controller and a power source operatively connected to the plurality of electromechanical actuators, for generating and modulating an electrical signal to energize the at least one actuator; a plurality of impedimetric sensors positioned proximate the plurality of electromechanical actuators, the impedimetric sensors comprising: a source electrode; a guard ring spaced from the source and surrounding the source in a circular form; and a probe electrode forming a semi-circular shape around a portion of the guard ring; and a computing device in communication with the wearable thorax percussion device and the plurality of impedimetric sensors, the computing device comprising: a processing device; and a memory device comprising: a data store comprising a lookup table of physiometric parameters; and instructions that, when executed by the processing device, cause the computing device to: a) determine a preliminary probe frequency range based on physiometric parameters of the patient and the lookup table; b) communicate instructions to the plurality of impedimetric sensors to sweep the preliminary probe frequency range in a vernier technique; c) identify a resonant point for the patient; d) communicate instructions to the wearable thorax percussion device to initiate a therapy protocol; e) monitor, with the plurality of impedimetric sensors, respiration cycles of the patient and efficacy of the therapy protocol by measuring impedance over time, segmenting into analysis periods that coincide with the respiration cycles of the patient, and recording impedance measurements during peak volume of end inspiration; f) create a measurement matrix representing impedance measurements between pairs of the impedimetric sensors, g) analyze the measurements to determine efficacy of the therapy protocol for a physiological area of the thorax associated with a sensor location; and h) based on the results of g, modulate or modify the therapy protocol by adjusting time, intensity, and/or frequency; and i) return to step e) and repeat until therapy has reached a measurable metric or has concluded.

The details of one or more techniques are set forth in the accompanying drawings and the description below. Other features, objects, and advantages of these techniques will be apparent from the description, drawings, and claims.

DETAILED DESCRIPTION

Figure 1:
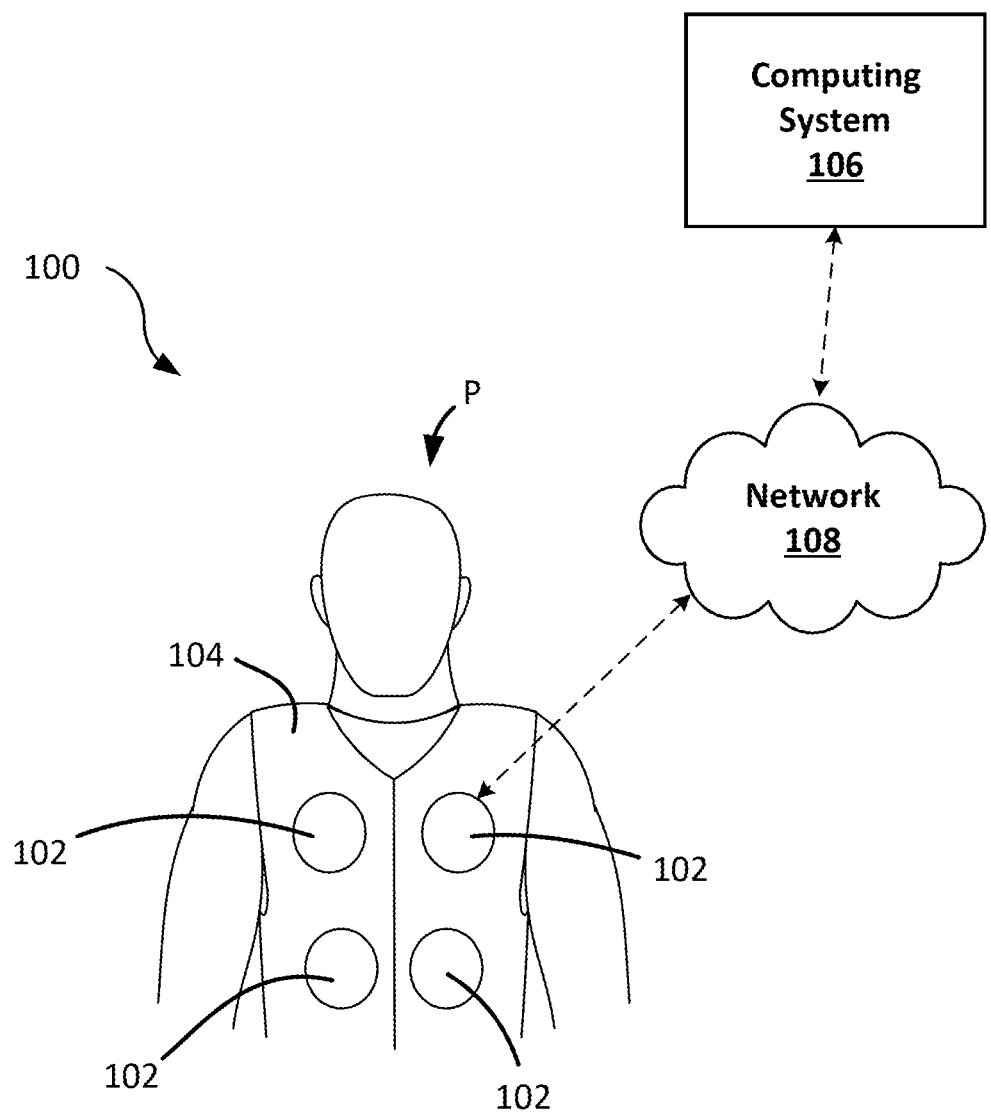
FIG. 1 is a schematic diagram illustrating an example system for administering pulmonary therapy to a patient.

The present disclosure is directed to systems and methods of monitoring medical therapies performed by wearable devices using electrical probes. In some embodiments, a pulmonary physiotherapy device implements a treatment protocol function gated and modulated using electrical impedance sensors and metrics.

Impedance Spectroscopy

Electrical impedance measures the amount of opposition that a circuit provides to a current when voltage is applied to the circuit. One technique for measuring electrical impedance involves applying a sinusoidal voltage waveform to the circuit to be measured and measure the returned current and phase shift. Often measurements from multiple different frequencies are taken to produce a precise measurement of impedance in any linear system.

In some instances, a frequency range of interest is continuously swept through as measurements are taken. For example, frequencies in the range of 100 hz to 2 Mhz might be swept for biological tissues, where ionic and dipolar forces predominate. Using this technique, an area known as the resonant point is located in a resultant plot of frequency against impedance. The resonant point indicates where the subject under test conditions transitions from operating as a capacitor to an inductor. The point and the region directly surrounding this point are of significant interest for physiological and biological measurements. The characteristics and order of the curve can demonstrate clinical condition and boundaries between fatty/dense tissue, profusion, air, bone, and the like. The curve can also distinguish between extracellular and intracellular fluids.

Pulmonary Disease

Pulmonary disease in general is a chronic inflammatory lung disease that causes obstructed airflow from the lungs. Symptoms include breathing difficulty, cough, mucus (sputum) production and wheezing. There are three primary forms of lung disease: airway diseases, lung tissue diseases, and lung circulation diseases. Airway diseases affect the tubes (airways) that carry oxygen and other gases into and out of the lungs. They usually cause a narrowing or blockage of the airways. Airway diseases include asthma, chronic obstructive pulmonary disease (COPD) and bronchiectasis. Lung tissue diseases affect the structure of the lung tissue.

Scarring or inflammation of the tissue makes the lungs unable to expand fully (restrictive lung disease). This makes it hard for the lungs to take in oxygen and release carbon dioxide. Pulmonary fibrosis and sarcoidosis are examples of lung tissue disease. Lung circulation diseases affect the blood vessels in the lungs. They are caused by clotting, scarring, or inflammation of the blood vessels. They affect the ability of the lungs to take up oxygen and release carbon dioxide. These diseases may also affect heart function. An example of a lung circulation disease is pulmonary hypertension.

Cystic fibrosis (CF) is a hereditary chronic disease affecting human patients that causes the buildup of thick, sticky mucous in the lungs and other parts of the body. If left untreated, the mucous can clog air ways, and lead to complications such as tissue inflammation or infection, or other symptoms such as coughing, phlegm, and compromised cardio-respiratory performance. CF in particular is a good target for mechanical therapies to release and expel secretions from the lungs.

Physiotherapy

Therapeutic medications for pulmonary disease are well known. Additional pulmonary therapy modalities include physiotherapy and mechanical manipulation of the subject. Lack of adherence to, or efficacy of, maintenance treatment including physiotherapy, is likely to be multifactorial, with factors including a large treatment burden or lack of understanding of the importance of this treatment. As pulmonary exacerbations may still occur even with optimum adherence, it is important for patients to continue maintenance therapies appropriately. Airway clearance is concomitant with airway surface liquid hydrators/mucolytics. These have specific electrical impedance characteristics.

One technique to manage CF is chest physiotherapy (CPT), which involves the manipulation of the patient's thorax to dislodge mucous buildup in the airways and encourage expectoration of the mucous. CPT may have to be performed in several sessions in a day, with each session lasting from between 10 to 45 minutes. CPT can be performed manually by therapists who use their hands to repeatedly percuss the patient's thorax. However, manually performed CPT can be physically and time demanding and should only be performed by a properly trained therapist. Alternatively, CPT can be performed using handheld or wearable mechanical devices. Wearable devices have the advantage over handheld devices of relieving the therapist or patient from having to manipulate the device during the therapy session.

One type of physiotherapy can be administered to patients at home using a wearable device that provides a mechanical means for CPT without the labor of a trained therapist. The device may be embodied in a form that is light weight, and ergonomically adapted to the anatomy of the thoracic region. An example of one such wearable device is described in FIG. 5.

The methods and systems described herein can be applied to other diseases and devices for treatment. Treatment for lymphedema, which is retention of water in tissues (common in cancer patients), can be treated with a peristaltic device. This massages the patient's legs to facilitate drainage of fluids. This is an example of a treatment that can be monitored with electrical impedance spectroscopy that is located in a part of the body other than the thorax.

Another example is a cough assist machine. A mechanical insufflation-exsufflation device helps to clear secretions such as mucus from a patient's lungs by simulating a cough. The machine increased air pressure to inflate the lungs and then rapidly changes to negative air pressure to mobilize secretions out of the airway. The patient's thorax can be monitored by impedance spectroscopy to determine if treatment needs to be modified or concluded.

FIG. 1 is a schematic diagram illustrating an example system 100 for administering pulmonary therapy to a patient P. While the figures show examples specific to pulmonary therapies, other types of devices could be used with the principles described, as mentioned above.

In the example shown in FIG. 1, the system 100 includes a plurality of impedimetric sensors 102 attached to a wearable medical therapy device 104. The impedimetric sensors 102 are in communication with a computing system 106 via a communications network 108. The impedimetric sensors 102 operate to measure impedance of tissues of the patient P wearing the medical therapy device 104. In some embodiments, the impedimetric sensors 102 are strategically placed on the medical therapy device 104 to position them over particular parts of the patient's body.

In this example, the wearable medical therapy device 104 is a vest that includes a plurality of electromechanical actuators configured to provide intermittent percussion to the patient's thorax. Operation of the electromechanical actuators and impedimetric sensors 102 is controlled by the computing system 106. In some embodiments, the computing system 106 is in direct, wired communication with the wearable garment 104. In some embodiments, the computing system 106 is a handheld electronic device attached to the garment 104 for controlling operation of therapy. In some embodiments, the computing system 106 operates as part of a smartphone, laptop, or other wireless communications enabled device that can be utilized to operate the garment 104 via Wi-Fi, Bluetooth, or other wireless communication methods.

Figure 2:
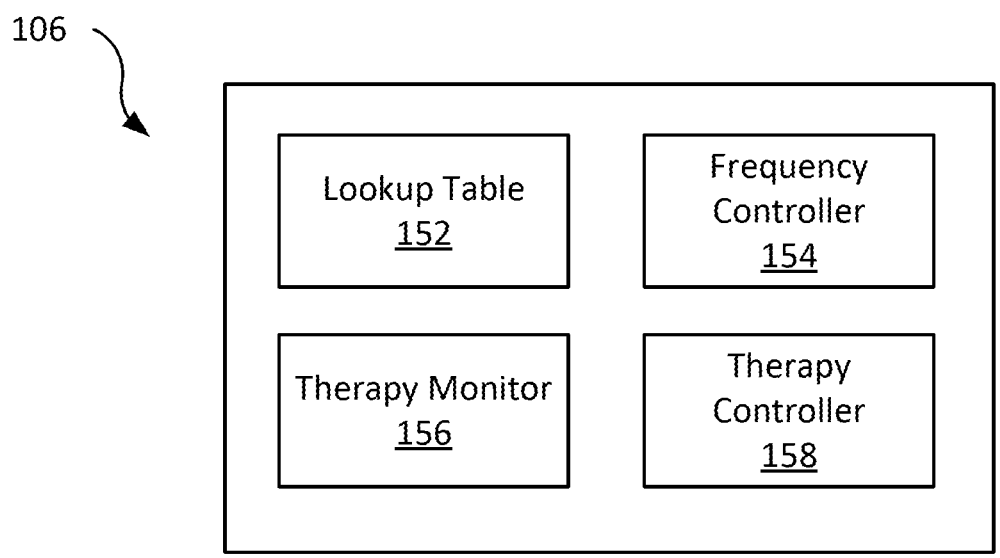
FIG. 2 is a more detailed schematic diagram of the computing system of FIG. 1.

FIG. 2 is a more detailed schematic diagram of the computing system 106 of FIG. 1. The computing system 106 operates to send instructions to impedimetric sensors 102 and other components of a wearable medical therapy device 104. The computing system 106 also operates to receive data from various electronic components of the wearable medical therapy device 104. The computing system 106 includes a lookup table 152, a frequency controller 154, a therapy monitor 156, and a therapy controller 158.

In some embodiments, one or more of the components of the computing system 106 are housed in a separate remote system in communication with the computing system 106. For example, the lookup table 152 could be located on a remote server instead of stored locally on the computing system 106. In some embodiments, all of the components of the computing system 106 are incorporated into one computing device such as a laptop, a smartphone, or a tablet. In some embodiments, the computing system 106 is housed in a remote control in wired or wireless communication with the wearable medical therapy device 104.

The lookup table 152 stores preliminary probe frequency ranges that correspond to patient physiometric parameters. In some embodiments, the patient's weight, height, age, and clinical standing are used to look up an appropriate preliminary probe frequency range for therapy. This provides an optimal signal response in the region between surface conduction of the mucosal membranes and cellular conduction. In some embodiments, the lookup table 152 is stored at a remote server and is accessed with a wireless connection to the computing system 106. One non-limiting example of a portion of one such lookup table for female patients is provided in Table 1 below.

TABLE 1

Female Patient Lookup Table

| Weight | Height | Age | Clinical standing | Current | Probe freq range |
|---|---|---|---|---|---|
| Average | Short | Pediatric | Fair health | 100 uA | 0-1 Mhz |
| Overweight | Short | Pediatric | Fair health | 250 uA | 0-1 Mhz |
| Average | Average | Pediatric | Fair health | 500 uA | 0-750 kHz |
| Overweight | Average | Pediatric | Fair health | 1 mA | 0-750 kHz |
| Average | Tall | Pediatric | Fair health | 1.250 mA | 0-500 kHz |
| Overweight | Tall | Pediatric | Fair health | 1.5 mA | 0-500 kHz |
| Average | Short | Early Adult | Fair health | 1 mA | 0-1 Mhz |
| Overweight | Short | Early Adult | Fair health | 1.250 mA | 0-1 Mhz |
| Average | Average | Early Adult | Fair health | 1.5 mA | 0-750 kHz |
| Overweight | Average | Early Adult | Fair health | 1.750 mA | 0-750 kHz |
| Average | Tall | Early Adult | Fair health | 2 mA | 0-500 kHz |
| Overweight | Tall | Early Adult | Fair health | 2.250 mA | 0-500 kHz |
| Average | Short | Older Adult | Fair health | 1.5 mA | 0-1 Mhz |
| Overweight | Short | Older Adult | Comorbidities | 1.75 mA | 0-1 Mhz |
| Average | Average | Older Adult | Comorbidities | 2 mA | 0-750 kHz |
| Overweight | Average | Older Adult | Chronic Disease | 2.250 mA | 0-750 kHz |
| Average | Tall | Older Adult | Chronic Disease | 2.250 mA | 0-500 kHz |
| Overweight | Tall | Older Adult | Chronic Disease | 2.250 mA | 0-500 kHz |

The frequency controller 154 operates to control the operation of the impedimetric sensors 102. The frequency controller 154 communicates instructions to the impedimetric sensors 102 to sweep the preliminary frequency range to find the resonant point. The frequency controller 154 also communicates instructions to the impedimetric sensors 102 to measure impedance between pairs of impedimetric sensors 102. Further detail on the functioning of the frequency controller 154 are provided in FIG. 4.

The therapy monitor 156 operates to monitor impedance measurements recorded by the impedimetric sensors 102 throughout a therapy session. Impedance is measured to determine respiration cycle and to determine treatment efficacy. Algorithms are employed to determine how well secretions are being cleared from the patient's lungs. As measurements are taken, the therapy monitor 156 determines whether intensity of therapy or duration of therapy should be modified. For example, if the algorithm calculates that the amount of extracellular fluid is not going down quickly enough, the intensity of the therapy may need to be increased. Alternatively, if the amount of extracellular fluid is going down very quickly, the therapy duration could be shortened.

The therapy controller 158 communicates instructions to the garment device to initiate and modify therapy protocols. Therapy protocols are selected based on a resonant point and order of a curve determined by sweeping an initial frequency range (performed by the frequency controller 154). Modifications are made to therapy protocols based on information received from the therapy monitor 156 indicating that a therapy session is more or less effective than expected.

Figure 3:
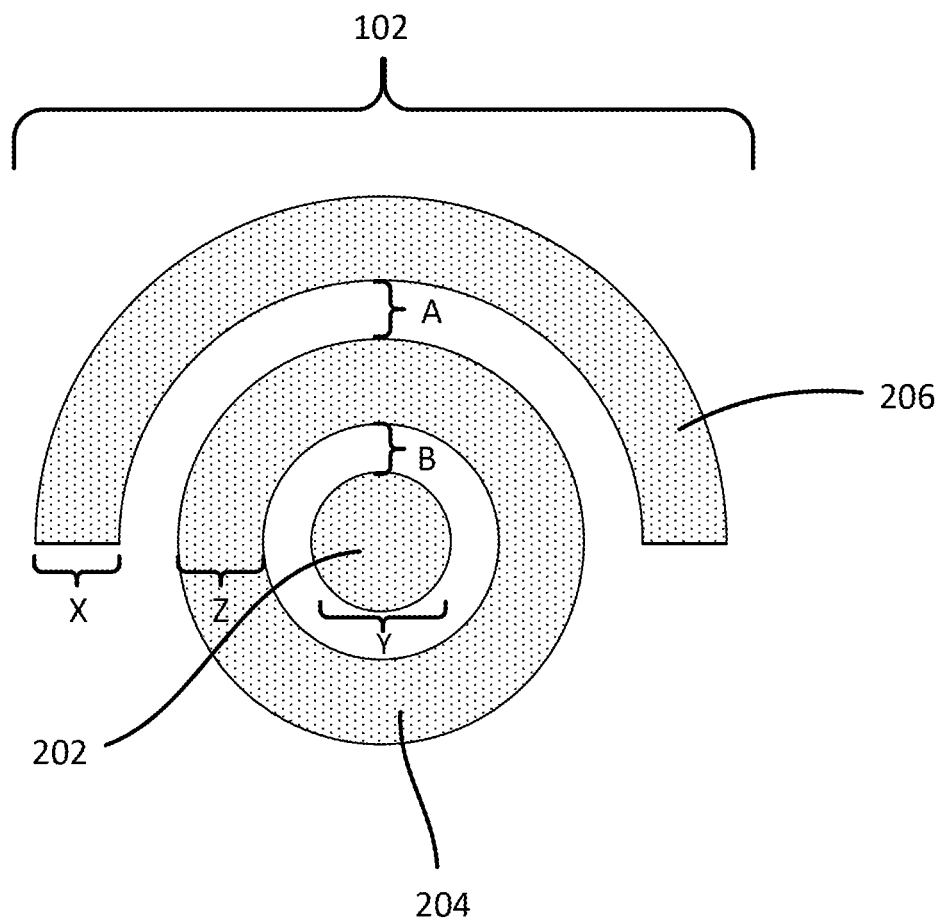
FIG. 3 is a schematic diagram of an example impedance sensor.

FIG. 3 is a schematic diagram of an example impedance sensor 102. The impedance sensor 102 includes a source 202, a guard ring 204, and a probe 206. Signal from the source 202 travels throughout all possible paths in the body and is recorded at the probe 206. The probe 206 is advantageously positioned within the same sensor, eliminating the need for separate sources and probes. To eliminate an overabundance of current coming from the source 202 directly to the probe 206, a guard ring surrounds the source 202. This allows for a source 202 of a first sensor to send current to a probe 206 of a second sensor. For example, using the probe layout shown in FIG. 6, one measurement could be from the source of the upper left sensor to the probe of the upper right sensor. Another measurement is from the source of the upper right sensor to the probe of the lower left sensor. All possible pairs are measured and recorded.

This sensor design is advantageous in that each sensor includes both a source and a probe, so that fewer electrodes are required. Additionally, the guard ring reduces the amount of signal that is recorded between the source and probe of the same sensor.

Figure 4:
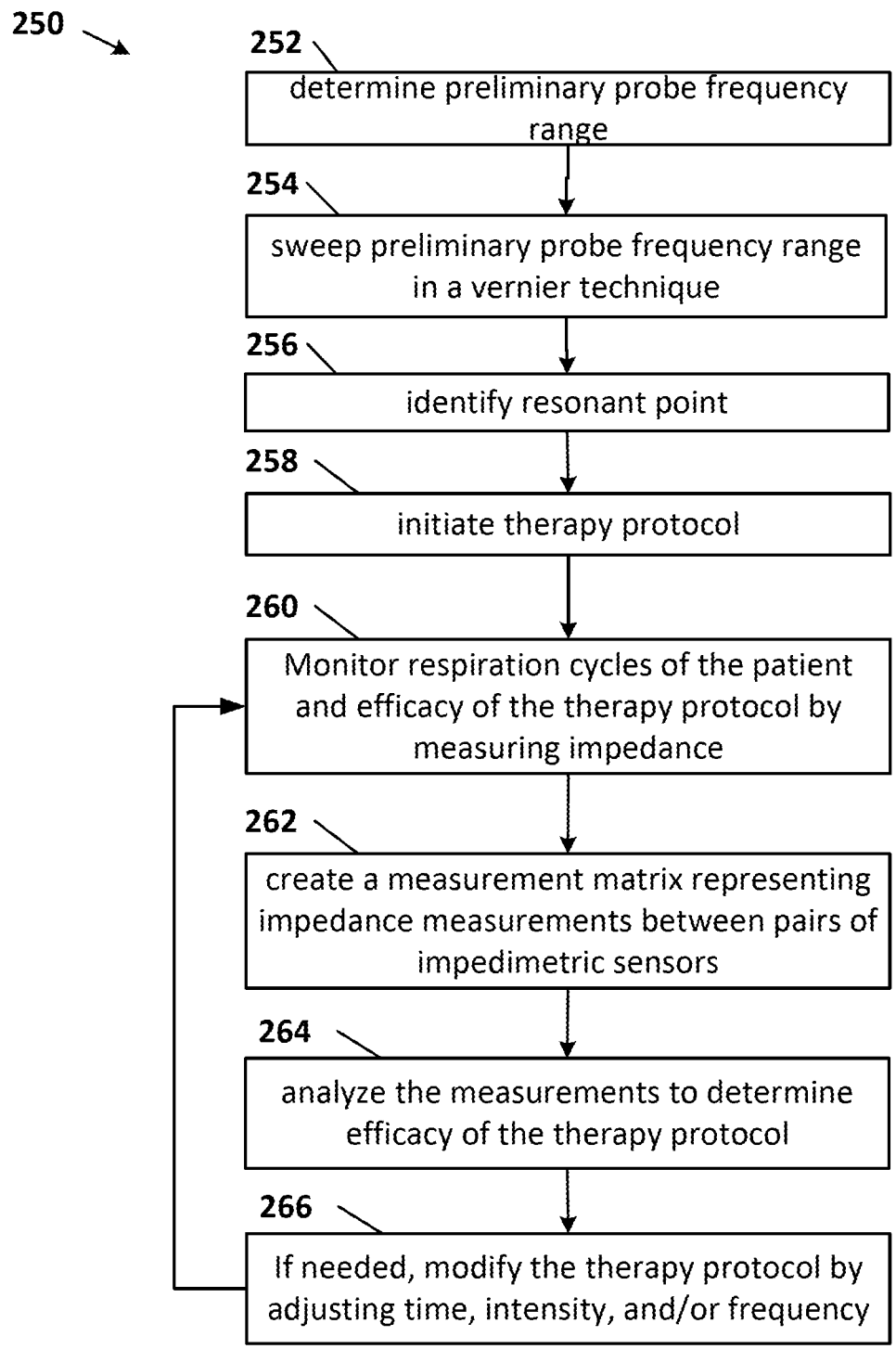
FIG. 4 is a flow chart of an example method of implementing a pulmonary physiotherapy protocol.

FIG. 4 is a flow chart of an example method 250 of implementing a pulmonary physiotherapy therapy protocol. In some embodiments, this method 250 is performed using the system 100 of FIG. 1.

At operation 252, a preliminary probe frequency range is determined. Physiometric parameters of a patient that is receiving therapy are used to look up the preliminary probe frequency range in a lookup table. In some embodiments, the physiometric parameters include weight, height, age, and clinical standing of the patient. The preliminary probe frequency is selected to provide an optimal signal response in the region between surface conduction of the mucosal membranes and cellular conduction.

At operation 254, the preliminary frequency range is swept. In some embodiments, this is performed in a vernier technique. In some embodiments, a time order-based frequency hopping technique is used. An example sweeping technique is described in greater detail with respect to FIG. 8. This step occurs after the wearable garment 104 is positioned on the patient so that the impedance sensors 102 are in contact with the patient's body. Thus, the subject for a wearable physiotherapy device is a patient's thorax.

At operation 256, the resonant point is localized. The resonant point represents the maximal impedance point. The resonant point is used to identify a curve in a graph plotting impedance against frequency. The order of the curve of that graph is used to determine a therapy protocol.

At operation 258, a therapy protocol is initiated. In some embodiments, a command is sent from a computing system to the therapy device. The computing system may be in wireless communication with the device or may be an attached remote control. The therapy protocol is selected based on the physiometric parameters of the patient as well as the results of the initial frequency sweep. The percussive actuators are prompted to begin actuating to percuss the patient's thorax according to the therapy protocol.

At operation 260, impedance measurements are taken with the impedance sensors. The sensors can use dry or wet electrodes that are in contact with the patient's body. These measurements are used to monitor the respiration cycle of the patient as well as the efficacy of the therapy. The respiration cycle is measured in order to determine when to record the impedance to monitor therapy. Measurements are segmented into analysis periods defined by the respiratory cycle. Measurements are taken at the same point in the respiratory cycle to ensure consistency. In some embodiments, measurements are made during peak volume of end inspiration.

Figure 6:
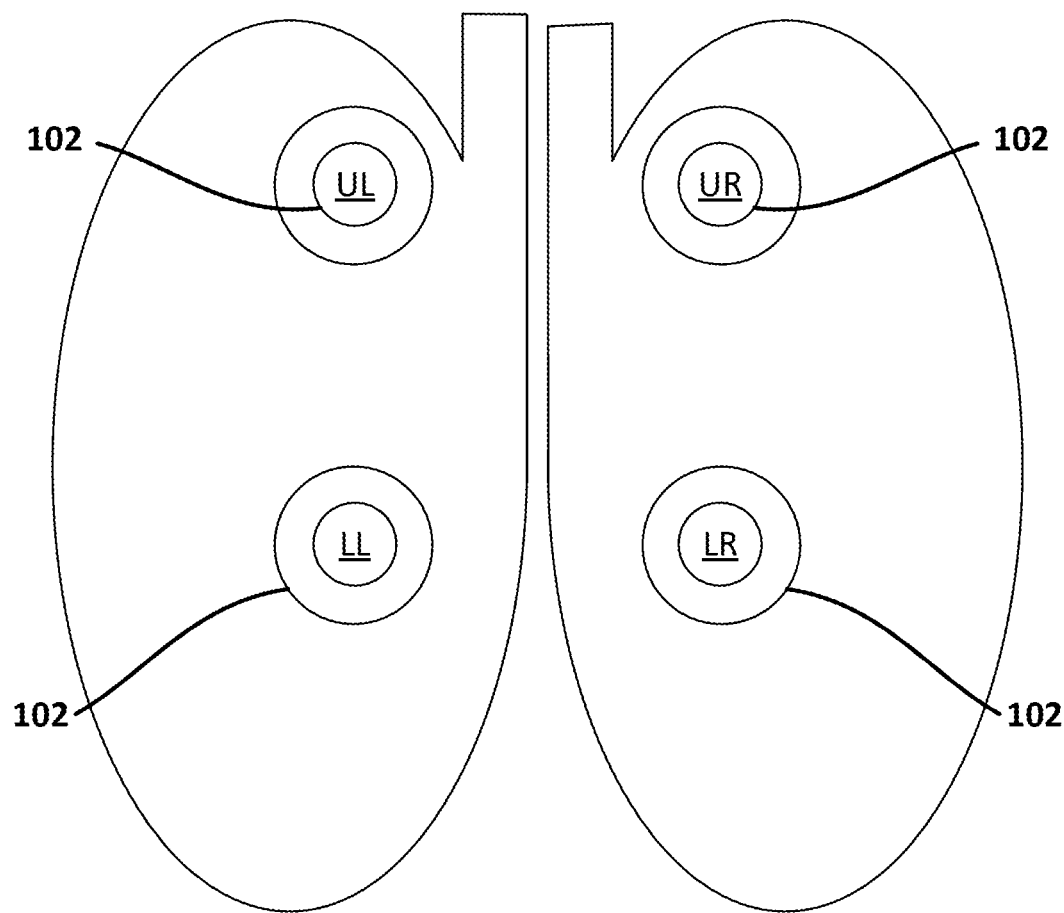
FIG. 6 is a schematic diagram illustrating example impedance sensor placement relative to a patient's lungs.

At operation 262, a measurement matrix is created that represents impedance measurements between each pair of impedimetric sensors. In some embodiments, there are four impedimetric sensors placed on four quadrants of the patient's lungs. The matrix can be constructed such that there is a measurement for each pair, where the pairs include: upper left to lower left, upper left to upper right, upper left to lower right, lower left to upper right, lower left to lower right, and upper right to lower right. A schematic illustrating the positions of the impedimetric sensors is illustrated in FIG. 6.

At operation 264, the measurements in the matrix are analyzed to determine efficacy of the therapy protocol. An algorithm is used to determine if intensity or duration of the therapy needs to be modified. For example, if the therapy is proving to be very effective, the duration of the therapy could be shortened. If the therapy is not progressing as quickly as expected, the duration could be extended or the intensity could be increased. In some embodiments, the algorithm can determine if therapy is recommended for the patient more or less frequently.

At operation 264, the therapy protocol is modified if needed. Then, the method returns to operation 260 and continues to cycle until the therapy protocol ends. Once the therapy has ceased, the patient can remove the wearable device 104.

Figure 5:
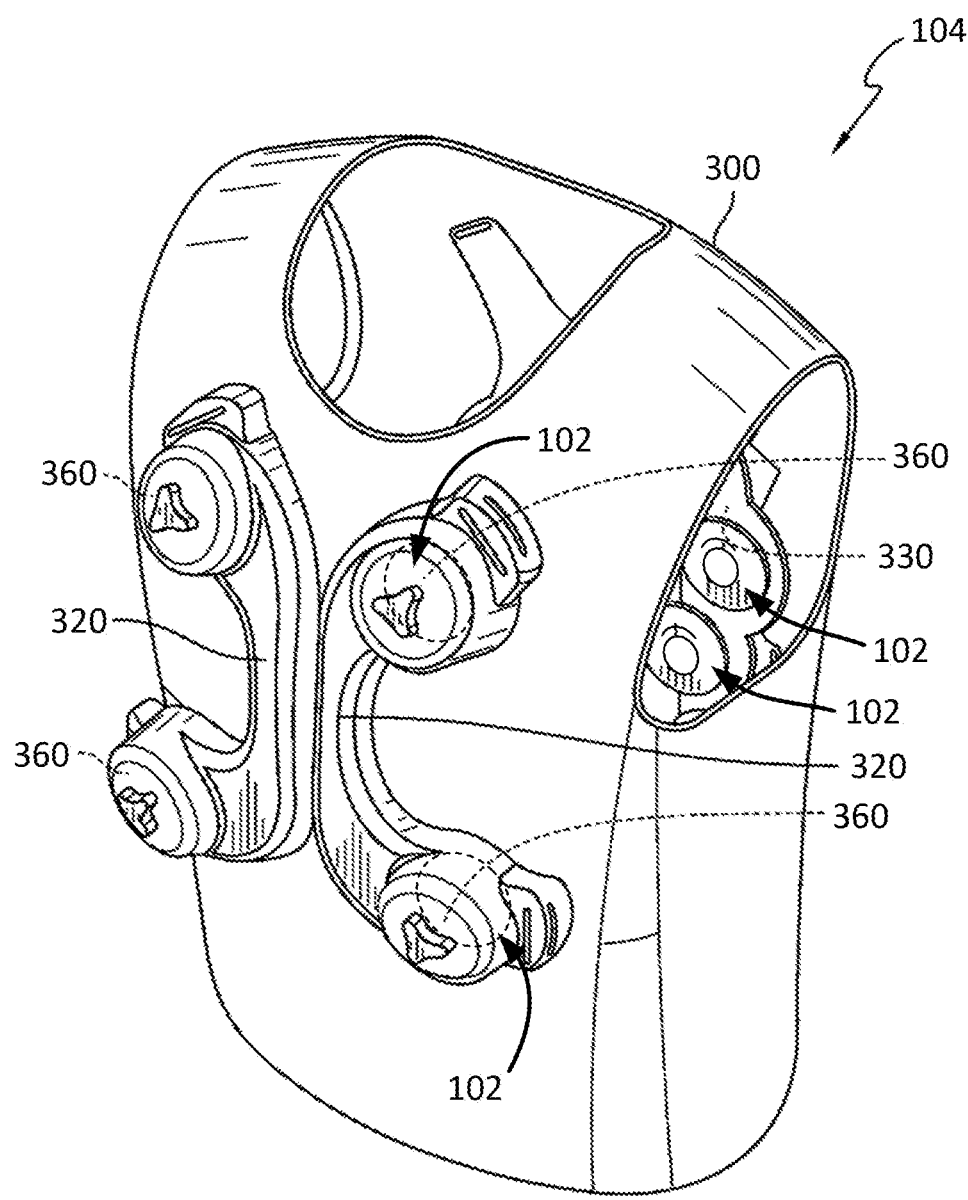
FIG. 5 illustrates an example of a wearable device that is used to treat pulmonary diseases.

FIG. 5 illustrates an example of a wearable device 104 that is used to treat pulmonary diseases such as cystic fibrosis (CF). In this example, the wearable device 104 takes the form of a vest 300 having a front frame element 320 and a rear frame element 330 interconnected with the vest 300 material. The frame elements 320, 330 include a plurality of electromechanical actuators 360 that are configured to provide percussion to a patient's thorax at particular locations. A plurality of impedimetric sensors 102 are attached to the vest 300 at the same locations as the electromechanical actuators 360. In this example, there are four electromechanical actuators 360 on the front frame element 320 and four electromechanical actuators 360 on the rear frame element 330. Thus, there are also four impedimetric sensors 102 on the front frame element 320 and four impedimetric sensors 102 on the rear frame element 330. The colocation of the impedimetric sensors 102 with the electromechanical actuators 360 ensures that impedimetric measurements are specific to each therapy location.

The vest 300 may comprise a variety of fasteners and adjustments to facilitate fitting the garment to a patient's thorax and positioning the frame elements 320, 330 on the user when the garment is worn. The front portion of the vest 300 may open and close with hook and loop fasteners, or other conventional fasteners such as zippers, clips or buttons, to permit the patient to don the vest 300. Additionally, or alternatively, the garment may be made of an elastic material to permit the user to slip the vest 300 on, or to adjust to individual body shapes, or both.

The vest 300 is preferably constructed of a light-weight, flexible and elastic material to accommodate the contours of the thorax. The vest 300 may separate the actuators 360 from the user to protect the user from pinch points of moving components or electronic components associated with the actuators 360. Alternatively, the garment may define openings through which the actuators may contact the user. In some embodiments, the impedimetric sensors 102 contact the skin of the patient. In some embodiments, the sensors utilize wet electrodes for better conductivity. In some embodiments, dry electrodes are used for greater patient comfort.

FIG. 6 illustrates example placement of impedance sensors 102 relative to a patient's lungs. This placement may be used for treatment of CF, COPD, or similar pulmonary disorders. In this example, sensors are placed over the upper left, upper right, lower right, and lower left of the patient's thorax. These placements correspond with the positions of electromechanical actuators that are attached to a garment such as the vest 300 of FIG. 5.

Figure 7:
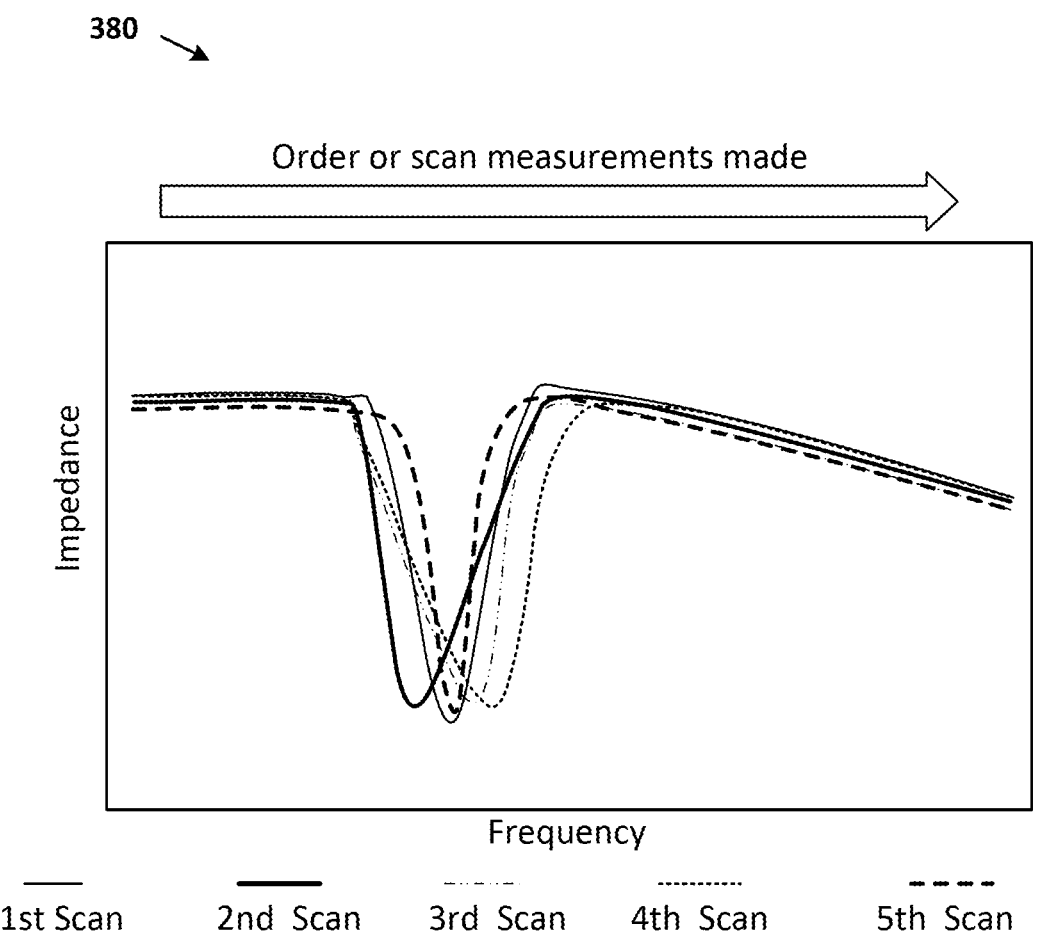
FIG. 7 illustrates a graph of impedance plotted against frequency for a conventional sequential method of sweeping a frequency range.

FIG. 7 illustrates a graph of impedance on the y-axis plotted against frequency on the x-axis. The graph shows five different scans of frequencies using an existing REIS sweeping mechanism. This sweeps through the frequencies in order from lowest to highest. The result is noisy data and signal acquisition artifacts. There is significant variability in the order of the curve obtained, thereby preventing the acquisition of a reliable resonant point. It is theorized that noise is the result of a conventional resonant technique. Biological tissues does not behave as a linear system, so it is difficult to simplify the model to one of series or parallel impedance.

Dielectric potentials and polarization potentials are alternatively exhausted and amplified by the presence of the AC electrical current itself. Ultimately, inducing a current at frequencies too close together does not allow the dielectric to recover from being exhausted. This causes variability and noise such that multiple reads need to be averaged to get a reliable result. However, this requires greater bandwidth in whichever system is employing the technique.

To address this problem, a time order frequency hopping technique is used to spread induced noise across the entire region of interest. This allows the complex chemistries under sample time to recover from electrochemical polarization in any one frequency region prior to being exposed to a similar frequency. To mitigate the loss of bandwidth forced in waiting for results—this algorithm can optionally be coupled with a vernier priority mechanism where the region of the curve you are interested in is rapidly localized and scanning intensified, while areas of little interest are interpolated. This modifies the procession of the scan appropriately.

Figure 8:
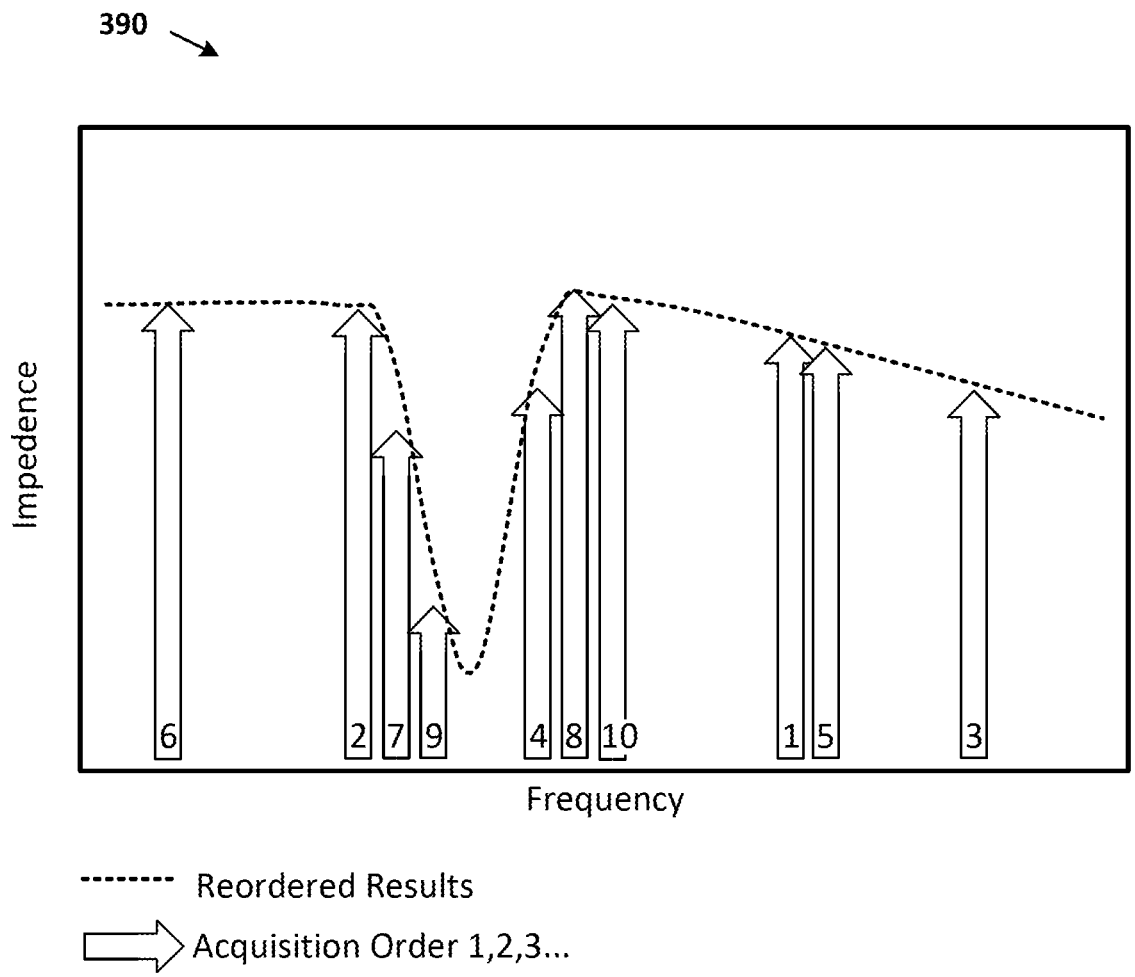
FIG. 8 illustrates a graph of impedance plotted against frequency for a time order frequency hopping technique of sweeping a frequency range.

FIG. 8 is a graph illustrating an example of how the time order frequency hopping technique could be implemented. As in FIG. 7, the frequency is plotted against impedance. "Sweeping" the frequency range of interest is done out of order instead of in sequential order. A first frequency is selected, measured, and then a second frequency a minimum distance away from the first is selected and measured, and so on. In this example, the first frequency selected for measurement is higher, the second is lower, the third is even higher than the first, the fourth is in the middle, and so on. Ultimately the entire range is sampled to provide measurements for all frequencies.

In some embodiments, an algorithm governs the operation of the modified frequency range sweep. The following are parameters of one such algorithm:
Region of exclusion (ROE: fixed or dynamic area not to be probed successively within "time window"; hz)
Time window (TW: the amount of time to wait before a frequency region can be probed again; units of samples)
Vernier Region Size (VRS: the size of the region of interest used for successive probes units of hz)
Random seed (RS: the frequency to start the probe, randomly obtained and gated by the other parameters; hz)

In an example base case there could be a ROE of 0, a TW of 0, and VRS of 100%. This would result in a simple random frequency hopping mechanism. The system would randomly probe the entire spectrum requested, then sort the results and reproduce a conventional curve. This yields some benefit. However, increasing the ROE and TW would prevent random duplicate localized hits, and thereby increase the specificity of results.

If implemented properly, these mechanisms both increase the specificity of the test and the effective bandwidth (total test time). All samples obtained are ordered (sorted) after they are measured. This puts them onto the conventional frequency spectrum, or nyquist diagram.

Figure 9:
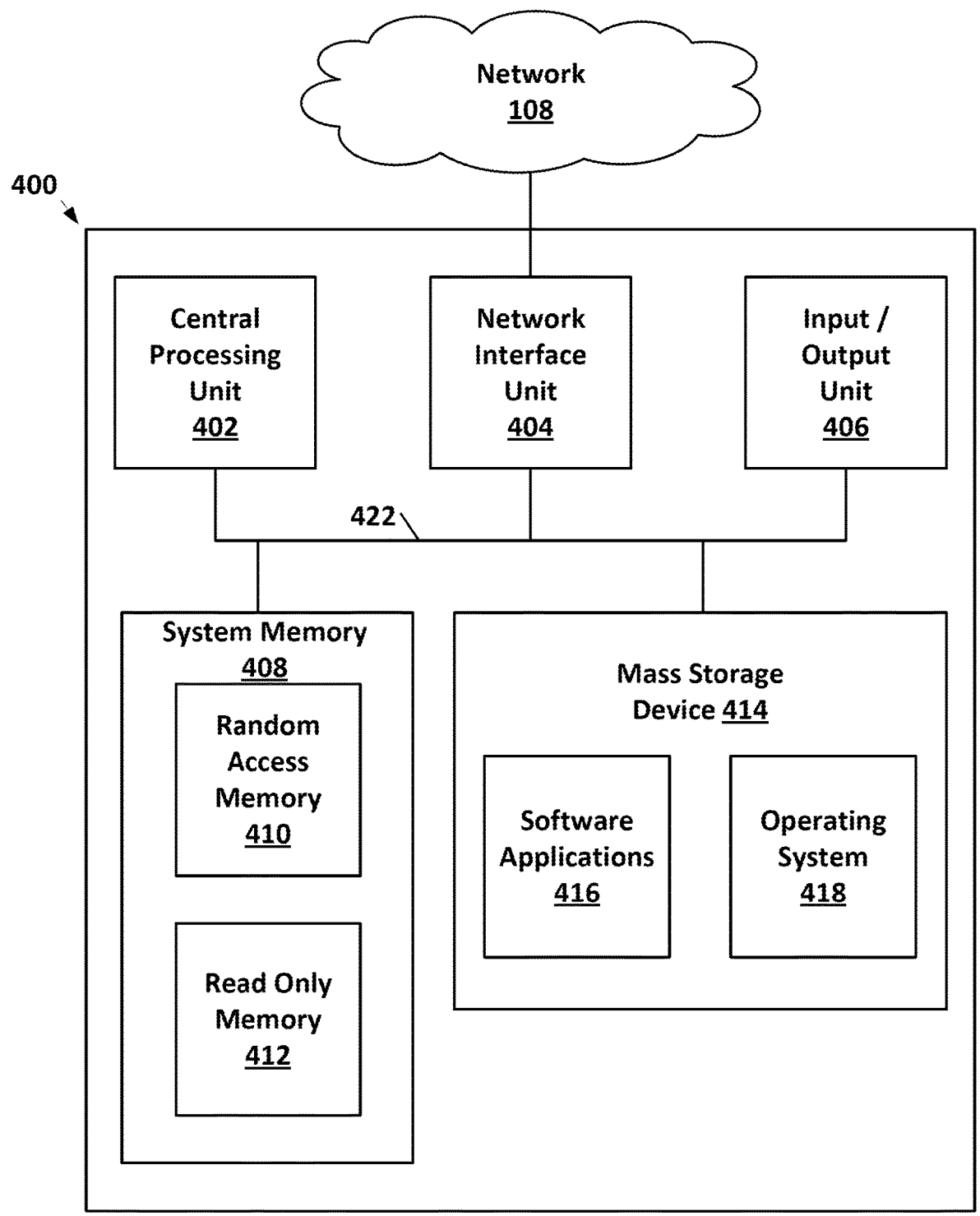
FIG. 9 is a schematic block diagram of an example computing device usable to implement aspects of the system of FIG. 1.

FIG. 9 is a block diagram illustrating an example of the physical components of a computing device 400. The computing device 400 could be any computing device utilized in conjunction with the example system 100 of FIG. 1 for administering pulmonary therapy to a patient. The computing device 400 could operate as part of the computing system 106 used to control operation of the wearable therapy device 104.

In the example shown in FIG. 9, the computing device 400 includes at least one central processing unit ("CPU") 402, a system memory 408, and a system bus 422 that couples the system memory 408 to the CPU 402. The system memory 408 includes a random access memory ("RAM") 410 and a read-only memory ("ROM") 412. A basic input/output system that contains the basic routines that help to transfer information between elements within the computing device 400, such as during startup, is stored in the ROM 412. The computing system 400 further includes a mass storage device 414. The mass storage device 414 can store software instructions and data such as therapy protocols and lookup tables.

The mass storage device 414 is connected to the CPU 402 through a mass storage controller (not shown) connected to the system bus 422. The mass storage device 414 and its associated computer-readable storage media provide non-volatile, non-transitory data storage for the computing device 400. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU 402 can read data and/or instructions. In certain embodiments, the computer-readable storage media comprises entirely non-transitory media.

Computer-readable storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device 400.

According to various embodiments, the computing device 400 can operate in a networked environment using logical connections to remote network devices through a network 108, such as a wireless network, the Internet, or another type of network. The computing device 400 may connect to the network 108 through a network interface unit 404 connected to the system bus 422. It should be appreciated that the network interface unit 404 may also be utilized to connect to other types of networks and remote computing systems. The computing device 400 also includes an input/output controller 406 for receiving and processing input from a number of other devices, including a touch user interface display screen, or another type of input device. Similarly, the input/output controller 406 may provide output to a touch user interface display screen or other type of output device.

As mentioned briefly above, the mass storage device 414 and the RAM 410 of the computing device 400 can store software instructions and data. The software instructions include an operating system 418 suitable for controlling the operation of the computing device 400. The mass storage device 414 and/or the RAM 410 also store software instructions, that when executed by the CPU 402, cause the computing device 400 to provide the functionality discussed in this document. For example, the mass storage device 414 and/or the RAM 410 can store software instructions that, when executed by the CPU 402, cause the computing system 400 to control operation of impedance sensors and pulmonary physiotherapy devices.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A medical therapy system, comprising:
   a wearable medical therapy device comprising:
   one or more electromechanical components configured to administer a medical therapy to a patient;
   a plurality of impedimetric sensors configured to monitor the medical therapy, each of the impedimetric sensors comprising a source, a guard ring, and a probe;
   an electronic controller and a power source operatively connected to the one or more electromechanical components and the plurality of impedimetric sensors, for generating and modulating an electrical signal to energize the one or more electromechanical components and the plurality of impedimetric sensors; and
   a computing device in communication with the wearable medical therapy device, the computing device comprising:
   a processing device; and
   a memory device comprising:
   a data store comprising a lookup table of physiometric parameters; and
   instructions that, when executed by the processing device, cause the computing device to:
   a) determine a preliminary frequency range based on physiometric parameters of a patient and a lookup table;
   b) communicate instructions to the plurality of impedimetric sensors to sweep the preliminary frequency range;
   c) receive impedimetric measurements from the impedimetric sensors and plot them against their respective frequencies;
   d) identify a resonant point and feature and shape characteristics of a curve generated from the patient in the plot;
   e) communicate instructions to the wearable medical therapy device to initiate a therapy protocol based on the curve;
   f) monitor, with the plurality of impedimetric sensors, efficacy of the therapy protocol by measuring impedance over time;
   g) create a measurement matrix representing impedance measurements between pairs of the impedimetric sensors;
   h) analyze the measurements to determine efficacy of the therapy protocol for a physiological area of the body associated with a sensor location;
   i) based on the results of step h), modulate or modify the therapy protocol; and
   j) return to step f) and repeat at least once.

2. The medical therapy system of claim 1, wherein the wearable medical therapy device is a pulmonary physiotherapy garment and the electromechanical components are electromechanical actuators configured to provide high frequency percussion to the patient's thorax.

3. The medical therapy system of claim 2, wherein the pulmonary physiotherapy garment comprises a vest and at least one frame element comprising a flat, rigid layer attached to the vest.

4. The medical therapy system of claim 1, wherein the impedimetric sensors comprise a substantially flat substrate having the source, guard ring, and probe arranged in a single plane, wherein the source is positioned at a central portion of the substrate, the guard ring is spaced from the source, forming a circumferential barrier around the source, and the probe is spaced from the guard ring and forming a semicircular shape around a portion of the guard ring.

5. The medical therapy system of claim 1, wherein the physiometric parameters comprise weight, height, age, and clinical standing of the patient.

6. The medical therapy system of claim 1, wherein the preliminary frequency range is swept in a time order based frequency hopping technique by selecting and measuring a plurality of frequencies within the preliminary frequency range one at a time, wherein each subsequent frequency is a minimum distance from the previous frequency.

7. The medical therapy system of claim 6, wherein the frequencies are selected using a vernier technique to increase selection of frequencies close to a region of interest.

8. The medical therapy system of claim 1, wherein the therapy protocol is modified by increasing or decreasing one or both of intensity and duration.

9. The medical therapy system of claim 1, wherein the wearable medical therapy device is a cough assist device configured to manipulate air pressure in the patient's lungs to expel secretions.

10. The medical therapy system of claim 1, wherein the wearable medical therapy device is a peristaltic device configured to facilitate drainage of fluids from the patient's legs.

11. A method of monitoring treatment efficacy of a body-worn medical therapy device, the method comprising:
   a) determining a preliminary probe frequency range based on physiometric parameters of a patient and a lookup table;
   b) communicating instructions to a plurality of impedimetric sensors to sweep the preliminary probe frequency range in a vernier technique;
   c) identifying a resonant point for the patient and determining an order of a curve for the impedance measurements;
   d) communicating instructions to the wearable thorax percussion device to initiate a therapy protocol, the therapy protocol comprising at least a duration and an intensity;
   e) monitoring, with the plurality of impedimetric sensors, respiration cycles of the patient and efficacy of the therapy protocol by measuring impedance over time, segmenting into analysis periods that coincide with the respiration cycles of the patient, and recording impedance measurements during peak volume of end inspiration;
   f) creating a measurement matrix representing impedance measurements between pairs of the impedimetric sensors,
   g) analyzing the measurements to determine efficacy of the therapy protocol for a physiological area of the thorax associated with a sensor location;
   h) based on the results of g, modulating or modifying the therapy protocol by adjusting one or more of duration and intensity; and
   i) returning to step e) and repeat at least once.

12. The method of claim 11, wherein the body-worn medical therapy device comprises a pulmonary physiotherapy vest for providing high frequency chest wall oscillation therapy to a patient.

13. The method of claim 12, wherein the vest comprises at least one frame element comprising a flat, rigid layer attached to the vest and a plurality of electromechanical actuators retained by the at least one frame element and configured to provide intermittent oscillations to one or more locations of the patient's chest wall to loosen lung secretions.

14. The method of claim 11, wherein the impedimetric sensors comprise a substantially flat substrate having the source, guard ring, and probe arranged in a single plane, wherein the source is positioned at a central portion of the substrate, the guard ring is spaced from the source, forming a circumferential barrier around the source, and the probe is spaced from the guard ring and forming a semi-circular shape around a portion of the guard ring.

15. The method of claim 11, wherein the preliminary frequency range is swept in a time order-based frequency hopping technique by selecting and measuring a plurality of frequencies within the preliminary frequency range one at a time, wherein each subsequent frequency is a minimum distance from the previous frequency.

16. A pulmonary physiotherapy system comprising:
a wearable thorax percussion device for dislodging mucous buildup in a set of airways of a human patient, the device comprising:
   a garment fitting over a thorax of the patient;
   at least one frame element comprising a flat, rigid layer attached to an external surface of the garment;
   a plurality of electromechanical actuators retained by the at least one frame element, wherein the electromechanical actuators are positioned to provide intermittent percussion to the thorax; and
   an electronic controller and a power source operatively connected to the plurality of electromechanical actuators, for generating and modulating an electrical signal to energize the at least one actuator;
a plurality of impedimetric sensors positioned proximate the plurality of electromechanical actuators, the impedimetric sensors comprising:
   a source electrode;
   a guard ring spaced from the source and surrounding the source in a circular form; and
   a probe electrode forming a semi-circular shape around a portion of the guard ring; and
a computing device in communication with the wearable thorax percussion device and the plurality of impedimetric sensors, the computing device comprising:
   a processing device; and
   a memory device comprising:
      a data store comprising a lookup table of physiometric parameters; and
      instructions that, when executed by the processing device, cause the computing device to:
         a) determine a preliminary probe frequency range based on physiometric parameters of a patient and a lookup table;
         b) communicate instructions to the plurality of impedimetric sensors to sweep the preliminary probe frequency range in a vernier technique;
         c) identify a resonant point for the patient;
         d) communicate instructions to the wearable thorax percussion device to initiate a therapy protocol;
         e) monitor, with the plurality of impedimetric sensors, respiration cycles of the patient and efficacy of the therapy protocol by measuring impedance over time, segmenting into analysis periods that coincide with the respiration cycles of the patient, and recording impedance measurements during peak volume of end inspiration;
         f) create a measurement matrix representing impedance measurements between pairs of the impedimetric sensors,
         g) analyze the measurements to determine efficacy of the therapy protocol for a physiological area of the thorax associated with a sensor location; and
         h) based on the results of g, modulate or modify the therapy protocol by adjusting time, intensity, and/or frequency; and
         i) return to step e) and repeat at least once.

* * * * *